United States Patent [19]

Weber et al.

[11] Patent Number: 5,354,911
[45] Date of Patent: Oct. 11, 1994

[54] PROCESS FOR THE PREPARATION OF UNSATURATED ETHERS

[75] Inventors: Jürgen Weber, Oberhausen; Peter Lappe, Dinslaken; Helmut Springer, Oberhausen, all of Fed. Rep. of Germany

[73] Assignee: Hoechst Aktiengesellschaft, Fed. Rep. of Germany

[21] Appl. No.: 178,634

[22] Filed: Jan. 7, 1994

Related U.S. Application Data

[63] Continuation of Ser. No. 23,489, Feb. 25, 1993, abandoned, which is a continuation of Ser. No. 804,843, Dec. 6, 1991, abandoned.

[30] Foreign Application Priority Data

Dec. 14, 1990 [DE]  Fed. Rep. of Germany ....... 4039950

[51] Int. Cl.$^5$ .............................................. C07C 41/28
[52] U.S. Cl. .................................................. 568/691
[58] Field of Search ..................................... 568/691

[56]  References Cited

U.S. PATENT DOCUMENTS 2,482,725  9/1949  Bramwyche et al. .............. 568/691
3,023,250  2/1962  Montagna et al. .................. 260/614

FOREIGN PATENT DOCUMENTS

| | | | |
|---|---|---|---|
| 217089 | 4/1987 | European Pat. Off. | C07C 41/28 |
| 299286 | 1/1989 | European Pat. Off. | C07C 43/16 |
| 327985 | 8/1989 | European Pat. Off. | C07C 43/16 |
| 3224033 | 1/1983 | Fed. Rep. of Germany | C07C 43/13 |
| 247669 | 7/1987 | German Democratic Rep. | C07C 43/14 |
| 2091259 | 7/1982 | United Kingdom | C07C 41/28 |

OTHER PUBLICATIONS

Chemical Abstracts, vol. 54, No. 22 (Nov. 25, 1960) Abstract 24452g

*Primary Examiner*—Howard T. Mars
*Attorney, Agent, or Firm*—Jordan B. Bierman

[57]  ABSTRACT

A process for the preparation of ethers of the formula $R^1-CR^2=CH-O-R^3$, in which $R^1$ and $R^3$ are each a radical having 1 to 6 carbon atoms and $R^2$ is hydrogen or a radical having 1 to 2 carbon atoms, by reaction of a diacetal of the formula $R^1-CHR^2-CH(-O-R^3)_2$ in the presence of a catalyst composed of an acid and an amine at elevated temperature in the liquid phase. The unsaturated ether of the above-mentioned formula is formed from the diacetal with elimination of an alcohol $R^3-OH$.

17 Claims, No Drawings

PROCESS FOR THE PREPARATION OF UNSATURATED ETHERS

This application is a continuation of application Ser. No. 08/023,489 filed Feb. 25, 1993 which in turn is a continuation of application Ser. No. 07/804,845 filed Dec. 6, 1991, both now abandoned.

This Application claims the priority of German Application P 40 39 950.8, filed Dec. 14, 1990.

The present invention relates to a process for the preparation of ethers of the formula $R^1-CR^2=CH-O-R^3$, in which $R^1$ is a radical having 1 to 6 carbon atoms, $R^2$ is hydrogen or a radical having 1 or 2 carbon atoms, and $R^3$ is a radical having 1 to 6 carbon atoms.

BACKGROUND OF THE INVENTION

Owing to their properties, ethers of the above-mentioned type are important for a number of industrial applications. They can be used as important building blocks and starting substances for the synthesis of specialty chemicals, pharmaceuticals, natural substances, and plant protection agents.

DE-PS 28 44 635 describes a process for the preparation of 2-propylpentene-4-al-1, in which the diacetal prepared from n-valeraldehyde and 2 mol of allyl alcohol is cleaved in the presence of an acid catalyst, for example p-toluenesulfonic acid, and the intermediate ether is thermally rearranged.

U.S. Pat. No. 3,023,250 relates to the preparation of halogen-substituted, unsaturated ethers by cleavage of corresponding 1,1-di-(2-haloalkoxy)alkanes in the presence of strong mineral acids or aromatic sulfonic acids which are not volatile under the reaction conditions. A relatively low-boiling nitrogen-containing base, for example an amine, is added inside a distillation column to the reaction mixture resulting from the cleavage reaction. The addition of the nitrogen-containing base serves to neutralize acidic compounds formed in the cleavage of the halogen-containing diacetal.

L. A. Yanovskaya et al. described in Otdel. Khim. Nauk 1960, 1246 to 1253 (Chem. Abstr. 54, 24452g (1960)) a process for the preparation of unsaturated ethers, in which an appropriate aldehyde diacetal is reacted with elimination of alcohol in the presence of a catalyst composed of p-toluenesulfonic acid and quinoline to give the unsaturated ether. The yields obtained, depending on the unsaturated ether to be prepared, are between 40 and 70%.

SUMMARY OF THE INVENTION

There is, therefore, a need for a process which, on the one hand, requires only a small outlay to carry it out and, on the other hand, is not restricted to the preparation of a few specific unsaturated ethers, but rather makes a large number of unsaturated ethers available. The process should further lead to a reduction in the undesired by-products and, at the same time, to an increase in the yields of desired end products.

This object is achieved by a process for the preparation of ethers of the formula $R^1-CR^2=CH-O-R^3$, in which $R^1$ is a radical having 1 to 6 carbon atoms, $R^2$ is hydrogen or a radical having 1 or 2 carbon atoms, and $R^3$ is a radical having 1 to 6 carbon atoms, which comprises reacting a diacetal of the formula $R^1-CHR^2-CH(-O-R^3)_2$ at elevated temperatures in the presence of a catalyst composed of an acid and an amine.

DETAILED DESCRIPTION OF THE INVENTION $R^1$ and $R^3$ are independently radicals having 1 to 6, preferably 1 to 4, and most preferably 1 to 3 carbon atoms. Examples of $R^1$ and $R^3$ which may be particularly mentioned are aliphatic straight or branched chain radicals. $R^1$ is advantageously methyl, ethyl, n-propyl, i-propyl, n-butyl, i-butyl, n-pentyl, i-pentyl, 2-methylbutyl, 3-methylbutyl, n-hexyl, or i-hexyl; preferably methyl, ethyl, n-propyl, i-propyl, n-butyl, or i-butyl; and most preferably methyl, ethyl, n-propyl, or i-propyl. $R^2$ includes hydrogen or a radical having 1 to 2 carbon atoms, in particular methyl or ethyl.

$R^3$ is advantageously a methyl, ethyl, n-propyl, i-propyl, n-butyl, i-butyl, n-pentyl, i-pentyl, 2-methylbutyl, 3-methylbutyl, n-hexyl or i hexyl radical, in particular a methyl, ethyl, n-propyl, i-propyl, n-butyl or i-butyl radical, preferably a methyl, ethyl, n-propyl or i-propyl radical.

The process according to the invention starts from a diacetal of the formula $R^1-CHR^2-CH(-O-R^3)_2$. Diacetals of this type are obtained by reaction of an aldehyde with an alcohol, the aldehyde group reacting with 2 alcohol molecules with the formation of water. This reaction is customarily carried out in the presence of acidic catalysts and the water of reaction formed is removed by azeotropic distillation using a suitable solvent. The catalyst used can be a mineral acid, for example sulfuric acid or phosphoric acid, or an aliphatic or aromatic sulfonic acid. Suitable solvents are all the organic solvents which form an appropriate azeotrope with water. Among these are aliphatic hydrocarbons, cyclohexane, cyclohexane derivatives, toluene and xylene. In many cases, cyclohexane has proven to be a particularly suitable solvent.

According to another variant, the aldehyde is reacted with the alcohol in the presence of the solvent and of the acidic catalyst at relatively low temperatures. The reaction mixture, which is obtained in heterogeneous form as a result of the solvent added, is neutralized and the water phase customarily obtained as the lower layer is separated. The solvent is then removed from the organic phase by distillation, optionally under reduced pressure. The distillation residue which remains, which already contains the desired diacetal of the aldehyde in high concentration, can be employed directly in the process according to the invention.

The diacetal is reacted in the presence of a catalyst composed of an acid and an amine. The acid requirement is very low; 0.00015 to 0.008, in particular 0.0002 to 0.006, preferably 0.00025 to 0.0015 mol of acid is employed per mol of diacetal. When selecting the acid, care should be taken that it has an adequate acid strength. The acid should have a pK of $\leq 2.5$, in particular $\leq 2.2$, most preferably $\leq 2.0$.

Suitable acids are phosphoric acid, its partially esterified derivatives, sulfuric acid, sulfuric acid hemiesters, and aliphatic or aromatic sulfonic acids, in particular aromatic sulfonic acids. Benzenesulfonic acid and toluenesulfonic acid, in particular p-toluenesulfonic acid, have proven to be highly suitable.

It has turned out to be advantageous not to employ the amine in any specific concentration, but to observe certain amount ratio limitations. The molar ratio of acid to amine should be 1:0.7 to 1:3.5, in particular 1:0.8 to 1:3, most preferably 1:1 to 1:2.

The amine functioning as the catalyst component should not be volatile under the reaction conditions and accordingly should have a boiling point which is at least 10° C., in particular 20° C., most preferably 30° C. above the boiling points of the reaction products formed. Amines which can be used are primary, secondary, and/or tertiary amines. The number of all the carbon atoms present in the amine is to be used as a criterion for selection of suitable amines. The amine should have altogether 8 to 30, in particular 9 to 24, most preferably 10 to 20 carbon atoms.

Suitable amines are cycloaliphatic and aliphatic amines, in particular straight-chain and/or branched aliphatic amines. Examples of amines are n-octyl-, n-nonyl-, n-decyl-, n-dodecyl-, 2-ethylhexyl-, i-nonyl-, 3,5,5-trimethylhexyl-, di-n-butyl-, di-i-butyl-, di-amyl-, di-n-hexyl-, di-n-octyl-, di-2-ethylhexyl-, di-i-nonyl-, tri-n-propyl-, tri-n-butyl-, tri-n-pentyl-, tri-n-hexyl-, tri-n-octyl-, tri-2-ethylhexyl-, tri-n-nonyl-, tri-i-nonyl- and tri-n-decylamine. In many cases, isononylamine, diamylamine, tri-n-butyl-amine, di-2-ethylhexylamine, and diisononylamine have proven particularly useful as the amine.

Amines are not understood to mean nitrogen-containing heterocyclic compounds, for example from the series comprising the pyridines, pyrimidines, pyrroles, pyrazoles, and their derivatives.

To carry out the process according to the invention, the catalyst system composed of the acid and the amine is added to the diacetal. The mixture is heated while mixing and the reaction products formed in the course of the reaction, namely the eliminated alcohol and the unsaturated ether of the formula $R^1$—$CR^2$=CH—O—$R^3$, are separated out. The process according to the invention can be carried out both batchwise—e.g. using a stirring vessel—and continuously—e.g. using a stirring vessel cascade, a bubble plate column, or a packed column. The reaction is carried out in the liquid phase, the temperature which is above the boiling point of the reaction products.

Possible diacetals of the formula $R^1$—$CHR^2$—CH(—O—$R^3$)$_2$ are open-chain diacetals which preferably have two identical acetal radicals. Examples are dimethyl acetals, diethyl acetals, di-n-propyl acetals, di-n-butyl acetals, di-i-butyl acetals, di-n-pentyl acetals, di-i-pentyl acetals, di-n-hexyl acetals, and di-i-hexyl acetals, all derived from aldehydes of the general formula $R^1$—$CHR^2$CHO, in which $R^1$ is a radical having 1 to 6 carbon atoms and $R^2$ is hydrogen or a radical having 1 or 2 carbon atoms.

Examples of diacetals of this type are acetaldehyde dimethyl acetal, acetaldehyde diethyl acetal, acetaldehyde dipropyl acetal, propionaldehyde dimethyl acetal, propionaldehyde diethyl acetal, propionaldehyde dipropyl acetal, propionaldehyde dibutyl acetal, butyraldehyde dimethyl acetal, butyraldehyde diethyl acetal, butyraldehyde dipropyl acetal, butyraldehyde dibutyl acetal, butyraldehyde dipentyl acetal, valeraldehyde dimethyl acetal, valeraldehyde diethyl acetal, valeraldehyde dipropyl acetal, valeraldehyde dibutyl acetal, valeraldehyde dipentyl acetal, isovaleraldehyde dimethyl acetal, isovaleraldehyde diethyl acetal, isovaleraldehyde dipropyl acetal, isovaleraldehyde dibutyl acetal, isovaleraldehyde dipentyl acetal, hexanal dimethyl acetal, hexanal diethyl acetal, hexanal dipropyl acetal, hexanal dibutyl acetal, hexanal dipentyl acetal, hexanal dihexyl acetal, 2-ethylhexanal dimethyl acetal, 2-ethylhexanal diethyl acetal, 2-ethylhexanal dipropyl acetal, 2-ethylhexanal dibutyl acetal, 2-ethylhexanal dipentyl acetal, and 2-ethylhexanal dihexyl acetal.

Propanal dimethyl acetal, propanal diethyl acetal, propanal diisopropyl acetal, propanal di-n-propyl acetal, butanal dimethyl acetal, butanal diethyl acetal, butanal diisopropyl acetal, butanal di-n-propyl acetal and valeraldehyde diethyl acetal have proven to be particularly suitable as the diacetal.

The reaction is customarily carried out at normal or slightly elevated pressure, but it is also possible to allow it to take place under reduced pressure. The addition of a solvent can be omitted.

The reaction temperature is selected depending on the pressure; it should customarily be a maximum of 220° C. to 240° C. In most cases, the reaction can be successfully carried out at temperatures of at most 200° C., in particular 180° C., most preferably 160° C. The catalyst system composed of the acid and the amine remains as a residue after separation of the reaction products formed and can optionally be employed again as a catalyst in the process according to the invention.

The examples which follow illustrate the invention without limiting it.

EXPERIMENTAL SECTION

I. Preparation of the starting substances (A): Preparation of propionaldehyde diethyl acetal To 553.2 g of ethanol, 900 g of cyclohexane, and 5.7 g of p-toluenesulfonic acid placed in a 4 liter three-necked flask fitted with a stirrer, dropping funnel, reflux condenser, and internal thermometer, 348.6 g of propionaldehyde are added with stirring in the course of 5 minutes. Owing to the acetal formation, which starts spontaneously, the internal temperature rises to about 40° C. The mixture is allowed to react at 40° C. for 30 minutes, a pH of 7.0 is then established in the reaction mixture, which is composed of a lower water phase and an upper organic phase, by addition of sodium hydroxide solution (20% aqueous solution) and the water phase is separated. To remove the low-boiling components, the organic phase is subjected to initial distillation at 1013 mbar and a bottom temperature up to 121° C.

After removal of the low-boiling components, 532.2 g of a product of the following composition (determined by gas-chromatographic analysis) remains (all percentages are by weight):

0.6% ethanol
0.1% propionaldehyde
3.8% cyclohexane
93.8% propionaldehyde diethyl acetal
1.7% other components (B): Preparation of n-butyraldehyde di-n-butyl acetal 889.5 g of n-butanol, 1500 g of cyclohexane, and 5.7 g of p-toluenesulfonic acid are placed in a 4 liter three-necked flask fitted with a stirrer, dropping funnel, reflux condenser, and internal thermometer. 432.7 g of n-butyraldehyde is added with stirring over a period of 5 minutes. Owing to the acetal formation which starts spontaneously, the internal temperature rises to about 35° C. The mixture is allowed to react at 35° C. to 40° C. for 30 minutes, a Ph of 7.0 is then established in the reaction mixture, which is composed of a lower water phase and an upper organic phase, by addition of sodium hydroxide solution (20% aqueous solution), and the water phase is separated. To remove the low-boiling components, the organic phase is subjected to initial distillation at 200 mbar and a bottom temperature up to 160° C.

After removal of the low-boiling components, 973.0 g of a product of the following composition (determined by gas-chromatographic analysis) remains (all percentages are by weight):
2.3% n-butanol
0.1% butyraldehyde
0.1% cyclohexane
95.7% n-butyraldehyde di-n-butyl acetal
1.8% other components.

(C): Preparation of 3-methylbutyraldehyde di-n-propyl acetal

To 841.4 g of n-propanol, 1750 g of cyclohexane, and 6.7 g of p-toluenesulfonic acid placed in a 4 liter three-necked flask fitted with a stirrer, dropping funnel, reflux condenser, and internal thermometer, 602.7 g of 3-methylbutyrladehyde is added with stirring over a period of 5 minutes. Owing to the acetal formation which starts spontaneously, the internal temperature rises to about 35° C. The mixture is allowed to react at 35° C. to 40° C. for 30 minutes, a pH of 7.0 is then established in the reaction mixture, which is composed of a lower water phase and an upper organic phase, by addition of sodium hydroxide solution (20% aqueous solution), and the water phase is separated. To remove the low-boiling components, the organic phase is subjected to initial distillation at 200 mbar and a bottom temperature up to 100° C.

After removal of the low-boiling components, 941.5 g of a product of the following composition (determined by gas-chromatographic analysis) remains (all percentages are by weight):
4.5% n-propanol
0.3% 3-methylbutyraldehyde
0.2% cyclohexane
91.9% 3-methylbutyraldehyde di-n-propyl acetal
3.1% other components (D): Preparation of 2-ethylbutyraldehyde dimethyl acetal 417.3 g of methanol, 1625 g of cyclohexane, and 6.2 g of p-toluenesulfonic acid are placed in a 4 liter three-necked flask fitted with a stirrer, dropping funnel, reflux condenser, and internal thermometer. 651.3 g of 2-ethylbutyraldehyde is added with stirring over a 5 minute period. Owing to the acetal formation which starts spontaneously, the internal temperature rises to about 32° C. The mixture is allowed to react at 40° C. for 30 minutes, a pH of 7.0 is then established in the reaction mixture, which is composed of a lower water phase and an upper organic phase, by addition of sodium hydroxide solution (20% aqueous solution), and the water phase is separated. To remove the low-boiling components, the organic phase is subjected to initial distillation at 200 mbar and a bottom temperature up to 105° C.

After removal of the low-boiling components, 760.7 g of a product of the following composition (determined by gas-chromatographic analysis) remains (all percentages are by weight):
0.1% cyclohexane
0.3% 2-ethylbutyraldehyde
97.9% 2-ethylbutyraldehyde dimethyl acetal
1.7% other components II. Preparation of the $\alpha,\beta$-unsaturated ethers IIa) Preparation of ethyl 1-propenyl ether

EXAMPLE 1

800 g of propionaldehyde diethyl acetal prepared as described in (A), 0.57 g of p-toluenesulfonic acid, and 1.13 g of di-2-ethylhexylamine are placed in a 2 liter round-bottomed flask fitted with a column (24 theoretical plates) and heated. The reaction products (ethanol and ethyl 1-propenyl ether), which are set free owing to the acetal cleavage, are distilled off at a reflux ratio of 3:1 and a pressure of 1013 mbar. The temperature at the head of the column is 67° C. to 70° C. The distillation is ended as soon as a bottom temperature of 220° C. is attained. 775.4 g of distillate are obtained. The yield of ethyl 1-propenyl ether is 98.2% of theoretical, based on the acetal employed.

COMPARISON EXAMPLE 1

The reaction is carried out as in Example 1, but without addition of di-2-ethylhexylamine. 748.5 g of distillate are obtained. The yield of ethyl 1-propenyl ether is only 34.0% of theoretical, based on the acetal employed.

EXAMPLE 2

The reaction is carried out as in Example 1, but with addition of 0.28 g of p-toluenesulfonic acid and 0.57 g of di-2-ethylhexylamine; 760.5 g of distillate are obtained. The yield of ethyl 1-propenyl ether is 95.9% of theoretical, based on the acetal employed.

EXAMPLE 3

The reaction is carried out as in Example 1, but with addition of 0.28 g of p-toluenesulfonic acid and 1.13 g of di-2-ethylhexylamine; 754.5 g of distillate are obtained. The yield of ethyl 1-propenyl ether is 85.5% of theoretical, based on the acetal employed.

EXAMPLE 4

The reaction is carried out as in Example 1, but with addition of 1.44 g of p-toluenesulfonic acid and 2.84 g of di-2-ethylhexylamine; 758.5 g of distillate are obtained. The yield of ethyl 1-propenyl ether is 93.2% of theoretical, based on the acetal employed.

EXAMPLE 5

The reaction is carried out as in Example 1, but with addition of 5.68 g of p-toluenesulfonic acid and 11.36 g of di-2-ethylhexylamine; 735.5 g of distillate are obtained. The yield of ethyl 1-propenyl ether is 89.1% of theoretical, based on the acetal employed.

EXAMPLE 6

The reaction is carried out as in Example 1, but with addition of 0.57 g of p-toluenesulfonic acid and 0.72 g of di-2-ethylhexylamine; 772.7 g of distillate are obtained. The yield of ethyl 1-propenyl ether is 97.8% of theoretical, based on the acetal employed.

EXAMPLE 7

The reaction is carried out as in Example 1, but with addition of 0.57 g of p-toluenesulfonic acid and 0.58 g of di-2-ethylhexylamine; 755.4 g of distillate are obtained. The yield of ethyl 1-propenyl ether is 91.7% of theoretical, based on the acetal employed.

EXAMPLE 8

The reaction is carried out as in Example 1, but with addition of 0.57 g of p-toluenesulfonic acid and 1.44 g of di-2-ethylhexylamine; 769.9 g of distillate are obtained. The yield of ethyl 1-propenyl ether is 97.6% of theoretical, based on the acetal employed.

EXAMPLE 9

The reaction is carried out as in Example 1, but with addition of 0.57 g of p-toluenesulfonic acid and 0.68 g of isononylamine (prepared by hydroformylation of diisobutylene and subsequent reductive amination); 773.8 g of distillate are obtained. The yield of ethyl 1-propenyl ether is 98.1% of theoretical, based on the acetal employed.

EXAMPLE 10

The reaction is carried out as in Example 1, but with addition of 0.57 g of p-toluenesulfonic acid and 1.28 g of diisononylamine (prepared by hydroformylation of diisobutylene and subsequent reductive amination); 708.3 g of distillate are obtained. The yield of ethyl 1-propenyl ether is 97.1% of theoretical, based on the acetal employed.

EXAMPLE 11

The reaction is carried out as in Example 1, but with addition of 0.57 g of p-toluenesulfonic acid and 0.75 g of diamylamine; 771.5 g of distillate are obtained. The yield of ethyl 1-propenyl ether is 97.8% of theoretical, based on the acetal employed.

EXAMPLE 12

The reaction is carried out as in Example 1, but with addition of 0.28 g of p-toluenesulfonic acid and 0.44 g of tri-n-butylamine; 765.3 g of distillate are obtained. The yield of ethyl 1-propenyl ether is 96.9% of theoretical based on the acetal employed.

The composition of the distillate obtained in each case in the preceding Examples (determined by gas chromatography) can be seen from Table 1 which follows.

as soon as a bottom temperature of 200° C. is attained. 770.2 g of distillate of the following composition (determined by gas chromatography) are obtained (all percentages are by weight):
37.4% n-butanol
0.1% n-butyraldehyde
0.1% cyclohexane
60.3% butyl 1-butenyl ether
1.1% n-butyraldehyde di-n-butyl acetal
1.0% other components The yield of butyl 1-butenyl ether is 95.8% of theoretical, based on the acetal employed.

COMPARISON EXAMPLE 2

The reaction is carried out as in Example 13, but without addition of di-2-ethylhexylamine; 763.1 g of distillate of the following composition (determined by gas chromatography) are obtained (all percentages are by weight):
23.1% n-butanol
0.1% cyclohexane
35.5% butyl 1-butenyl ether
39.8% n-butyraldehyde di-n-butyl acetal
1.5% other components The yield of butyl 1-butenyl ether is 55.8% of theoretical, based on the acetal employed.

EXAMPLE 14

The reaction is carried out as in Example 13, but with addition of 0.38 g of p-toluenesulfonic acid and 0.76 g of di-2-ethylhexylamine; 778.2 g of distillate of the following composition (determined by gas chromatography) are obtained (all percentages are by weight):
37.8% n-butanol
0.1% n-butyraldehyde
0.1% cyclohexane
61.3% butyl 1-butenyl ether
0.2% n-butyraldehyde di-n-butyl acetal
0.5% other components

TABLE

| Example | 1 | 2 | 3 | 4 | 5 | 6 | 7 | 8 | 9 | 10 | 11 | 12 | |
| --- | --- | --- | --- | --- | --- | --- | --- | --- | --- | --- | --- | --- | --- |
| Comparison Example | | | | | | | | | | | | | 1 |
| Composition* (% by weight) | | | | | | | | | | | | | |
| Ethanol | 33.7 | 33.6 | 30.3 | 32.7 | 32.1 | 33.7 | 32.3 | 33.7 | 33.7 | 33.6 | 33.7 | 33.7 | 12.5 |
| Propanal | 0.2 | 0.2 | 0.2 | 1.4 | 1.5 | 0.2 | 0.3 | 0.2 | 0.2 | 0.2 | 0.2 | 0.2 | 0.2 |
| Cyclohexane | 3.9 | 4.0 | 4.1 | 0.6 | 0.7 | 3.9 | 3.8 | 3.8 | 3.7 | 3.9 | 3.8 | 3.7 | 4.1 |
| Ethyl 1-propenyl ether | 61.9 | 61.7 | 55.4 | 61.0 | 60.1 | 61.9 | 59.3 | 62.0 | 62.0 | 61.8 | 62.0 | 61.9 | 22.2 |
| Propanal diethyl acetal | 0.1 | 0.3 | 9.5 | 2.9 | 3.8 | 0.1 | 3.8 | 0.1 | 0.1 | 0.1 | 0.1 | 0.1 | 59.9 |
| Other components | 0.2 | 0.2 | 0.5 | 1.4 | 1.8 | 0.2 | 0.5 | 0.2 | 0.3 | 0.4 | 0.2 | 0.4 | 1.1 |
| Distillate (g) | 775.4 | 760.5 | 754.5 | 758.5 | 735.5 | 772.7 | 755.4 | 769.9 | 773.8 | 708.3 | 771.5 | 765.3 | 748.5 |
| Yield** (% of theoretical) | 98.2 | 95.9 | 85.5 | 93.2 | 89.1 | 97.8 | 91.7 | 97.6 | 98.1 | 97.1 | 97.8 | 96.9 | 34.0 |

*Composition determined by gas-chromatographic analysis
**Based on diacetal employed IIb) Preparation of butyl 1-butenyl ether

EXAMPLE 13

800 g of n-butyraldehyde di-n-butyl acetal, prepared as described in (B), 0.19 g of p-toluenesulfonic acid, and 0.38 g of di-2-ethylhexylamine are placed in a 2 liter round-bottomed flask fitted with a column (24 theoretical plates) and heated. The reaction products (n-butanol and butyl 1-butenyl ether) set free owing to the acetal cleavage are distilled off at a reflux ratio of 0.5:1 and a pressure of 200 mbar. The temperature at the head of the column is 74° C. to 81° C. The distillation is ended The yield of butyl 1-butenyl ether is 98.3% of theoretical, based on the acetal employed.

IIc) Preparation of 3-methyl-1-butenyl propyl ether

EXAMPLE 15

800 g of 3-methylbutyraldehyde di-n-propyl acetal, prepared as described in (C), 0.2 g of p-toluene-sulfonic acid, and 0.39 g of di-2-ethylhexylamine are placed in a 2 liter round-bottomed flask fitted with a column (24 theoretical plates) and heated. The reaction products (n-propanol and 3-methyl-1-butenyl propyl ether) set free owing to the acetal cleavage are distilled off at a reflux ratio of 1:1 and a pressure of 200 mbar. The temperature at the head of the column is 60° C. to 63° C. The distillation is ended as soon as a bottom temperature of 200° C. is attained. 775.6 g of distillate of the following composition (determined by gas chromatography) are obtained (all percentages are by weight):

34.7% n-propanol
0.2% 3-methylbutyraldehyde
0.2% cyclohexane
63.9% 3-methyl-1-butenyl propyl ether
0.2% 3-methylbutyraldehyde di-n-propyl acetal
0.8% other components The yield of 3-methyl-1-butenyl propyl ether is 99.0% of theoretical, based on the acetal employed.

COMPARISON EXAMPLE 3

The reaction is carried out as in Example 15, but without addition of di-2-ethylhexylamine; 765.5 g of distillate of the following composition (determined by gas chromatography) are obtained (all percentages are by weight):

32.0% n-propanol
0.3% 3-methylbutyraldehyde
0.2% cyclohexane
58.2% 3-methyl-1-butenyl propyl ether
6.5% 3-methylbutyraldehyde di-n-propyl acetal
2.8% other components The yield of 3-methyl-1-butenyl propyl ether is 89.0% of theoretical, based on the acetal employed.

IId) Preparation of 2-ethyl-1-butenyl methyl ether

EXAMPLE 16

720 g of 2-ethylbutyraldehyde dimethyl acetal, prepared as described in (D), 0.48 g of p-toluenesulfonic acid, and 0.96 g of 2-ethylhexylamine are placed in a 2 liter round-bottomed flask fitted with a column (24 theoretical plates) and heated. The reaction products (methanol and 2-ethyl-1-butenyl methyl ether) set free owing to the acetal cleavage are distilled off at a reflux ratio of 10:1 and a pressure of 1013 mbar. The temperature at the head of the column is 104° C. to 115° C. The distillation is ended as soon as a bottom temperature of 200° C. is attained. 692.5 g of distillate of the following composition (determined by gas chromatography) are obtained (all percentages are by weight):

21.4% methanol
0.1% cyclohexane
0.4% ethylbutyraldehyde
77.1% 2-ethyl-1-butenyl methyl ether
0.1% 2-ethylbutyraldehyde dimethyl acetal
0.9 other components The yield of 2-ethyl-1-butenyl methyl ether is 97.0% of theoretical, based on the acetal employed.

COMPARISON EXAMPLE 4

The reaction is carried out as in Example 16, with 0.48 g of p-toluenesulfonic acid, but without addition of 2-ethylhexylamine; 683.2 g of distillate of the following composition (determined by gas chromatography) are obtained (all percentages are by weight):

19.6% methanol
0.1% cyclohexane
0.4% 2-ethylbutyraldehyde
70.1% 2-ethyl-1-butenyl methyl ether
8.1% 2-ethylbutyraldehyde dimethyl acetal
1.7% other components The yield of 2-ethyl-1-butenyl methyl ether is 87.0% of theoretical, based on the acetal employed.

While only a limited number of specific embodiments have been expressly disclosed, it is, nonetheless, to be broadly construed, and not to be limited except by the character of the claims appended hereto.

What we claim is:

1. A process for the preparation of ethers of the formula $R^1-CR^2=CH-O-R^3$, wherein $R^1$ is an alkyl radical having 1 to 6 carbon atoms, $R^2$ is hydrogen or an alkyl radical having 1 or 2 carbon atoms, and $R^3$ is an alkyl radical having 1 to 6 carbon atoms, said process comprising reacting a diacetal of the formula $R^1-CHR^2-CH(-O-R^3)_2$, at an elevated temperature, in the presence of a catalyst composed of an acid having a pK value not exceeding 2.5, and a cycloaliphatic or aliphatic amine having 8 to 30 carbon atoms, said acid and said amine being present in a molar ratio of 1:0.7 to 1:3.5.

2. The process of claim 1 wherein said acid is present in an amount of 0.00015 to 0.008 tools per mol of diacetal.

3. The process of claim 2 wherein said amount is 0.00025 to 0.0015 mols per mol of diacetal.

4. The process of claim 1 wherein $R^1$ and $R^3$ are radicals each selected from the group consisting of alkyls having straight or branched chains.

5. The process of claim 1 wherein said pK does not exceed 2.0.

6. The process of claim 1 wherein said acid is selected from the group consisting of phosphoric, partially esterified derivatives thereof, sulfuric, hemi esters thereof, aromatic sulfonic, and aliphatic sulfonic.

7. The process of claim 6 wherein said acid is aromatic sulfonic or aliphatic sulfonic.

8. The process of claim 7 wherein said acid is benzene sulfonic or toluene sulfonic.

9. The process of claim 1 wherein said molar ratio is 1:1 to 1:2.

10. The process of claim 1 wherein said amine is non-volatile under conditions of said process.

11. The process of claim 1 wherein said amine is selected from the group consisting of n-octyl, n-nonyl-, n-decyl-, n-dodecyl-, 2-ethylhexyl-, i-nonyl-, 3,5,5-trimethylhexyl-, di-n-butyl-, di-i-butyl-, diamyl-, di-n-hexyl-, di-n-octyl-, di-2-ethylhexyl-, di-i-nonyl-, tri-n-propyl-, tri-n-butyl-, tri-n-pentyl-, tri-n-hexyl-, tri-n-octyl-, tri-2-ethylhexyl-, tri-n-nonyl-, tri-i-nonyl- and tri-n-decylamine.

12. The process of claim 11 wherein said amine is selected from the group consisting of isononylamine, diamylamine, tri-n-butyl-amine, di-2-ethylhexylamine, and diisonnonylamine.

13. The process of claim 1 wherein said diacetal is selected from the group consisting of dimethyl acetals, diethyl acetals, di-n-propyl acetals, di-n-butyl acetals, di-i-butyl acetals, di-n-pentyl acetals, di-i-pentyl acetals, di-n-hexyl acetals, and di-i-hexyl acetals, all of aldehydes of the general formula $R^1-CHR^2-CHO$, in which $R^1$ is a radical having 1 to 6 carbon atoms and $R^2$ is hydrogen or a radical having 1 or 2 carbon atoms.

14. The process of claim 1 wherein said diacetal is selected from the group consisting of acetaldehyde dimethyl acetal, acetaldehyde diethyl acetal, acetaldehyde dipropyl acetal, proplonaldehyde dimethyl acetal, propionaldehyde diethyl acetal, propionaldehyde dipropyl acetal, propionaldehyde dibutyl acetal, butyraldehyde dimethyl acetal, butyraldehyde diethyl acetal, butyraldehyde dipropyl acetal, butyraldehyde dibutyl acetal, butyraldehyde dipentyl acetal, valeraldehyde dimethyl acetal, valeraldehyde diethyl acetal, valeraldehyde dipropyl acetal, valeraldehyde dibutyl acetal, valeraldehyde dipentyl acetal, isovaleraldehyde dimethyl acetal, isovaleraldehyde diethyl acetal, isovaleraldehyde dipropyl acetal, isovaleraldehyde dibutyl acetal, Isovaleraldehyde dipentyl acetal, hexanal dimethyl acetal, hexanal diethyl acetal, hexanal dipropyl acetal, hexanal dibutyl acetal, hexanal dipentyl acetal, hexanal dihexyl acetal, 2-ethylhexanal dimethyl acetal, 2-ethylhexanal diethyl acetal, 2-ethylhexanal dipropyl acetal, 2-ethylhexanal dibutyl acetal, 2-ethylhexanal dipentyl acetal, and 2-ethylhexanal dihexyl acetal.

15. The process of claim 1 which is carried at a temperature not exceeding 220° C. to 240° C.

16. The process of claim 15 wherein said temperature does not exceed 200° C.

17. The process of claim 1 which is carried out at a temperature above a boiling temperature of said reaction products.

* * * * *